US010619143B2

(12) United States Patent
Kim et al.

(10) Patent No.: US 10,619,143 B2
(45) Date of Patent: Apr. 14, 2020

(54) METHOD AND PRODUCING BOTULINUM TOXIN

(71) Applicant: DAEWOONG CO., LTD., Gyeonggi-do (KR)

(72) Inventors: Kyoung-Yun Kim, Jeollabuk-do (KR); Chung Sei Kim, Seoul (KR); Myung Seob Kim, Gyeonggi-do (KR); Hye-Young Sul, Gyeonggi-do (KR)

(73) Assignee: DAEWOONG CO., LTD., Gyeonggi-Do (KR)

( * ) Notice: Subject to any disclaimer, the term of this patent is extended or adjusted under 35 U.S.C. 154(b) by 0 days.

(21) Appl. No.: 15/758,042

(22) PCT Filed: Nov. 23, 2016

(86) PCT No.: PCT/KR2016/013506
§ 371 (c)(1),
(2) Date: Mar. 7, 2018

(87) PCT Pub. No.: WO2017/095062
PCT Pub. Date: Jun. 8, 2017

(65) Prior Publication Data
US 2018/0251741 A1 Sep. 6, 2018

(30) Foreign Application Priority Data
Nov. 30, 2015 (KR) .................. 10-2015-0168196

(51) Int. Cl.
*C12N 9/52* (2006.01)
*B01D 15/36* (2006.01)
*B01D 61/14* (2006.01)
*B01D 61/58* (2006.01)
*C07K 14/33* (2006.01)

(52) U.S. Cl.
CPC ............. *C12N 9/52* (2013.01); *B01D 15/362* (2013.01); *B01D 15/363* (2013.01); *B01D 61/145* (2013.01); *B01D 61/147* (2013.01); *B01D 61/58* (2013.01); *C07K 14/33* (2013.01); *C12Y 304/24069* (2013.01); *B01D 2315/16* (2013.01)

(58) Field of Classification Search
CPC ...................................................... C12N 9/52
See application file for complete search history.

(56) References Cited

U.S. PATENT DOCUMENTS

| 7,452,697 B2 | 11/2008 | Luo et al. |
| 2005/0238669 A1 | 10/2005 | Xiang et al. |
| 2011/0008843 A1* | 1/2011 | Ton .................. C07K 14/33 435/71.3 |
| 2012/0088732 A1 | 4/2012 | Bigalke et al. |
| 2013/0071331 A1 | 3/2013 | Chung et al. |
| 2013/0156756 A1 | 6/2013 | Schulze et al. |
| 2015/0184141 A1 | 7/2015 | Ton et al. |
| 2015/0337281 A1 | 11/2015 | Kim et al. |

FOREIGN PATENT DOCUMENTS

| JP | 06-192296 A | 7/1994 |
| JP | 06-199296 A | 7/1994 |
| JP | 2003503343 A | 1/2003 |
| JP | 2008531046 A | 8/2008 |
| KR | 10-2009-0091501 A | 8/2009 |
| KR | 10-1339349 B1 | 12/2013 |
| KR | 10-11339349 B1 | 12/2013 |
| WO | 2006096163 A1 | 9/2006 |
| WO | WO2011050072 A1 | 4/2011 |
| WO | WO2015016462 A1 | 2/2015 |

OTHER PUBLICATIONS

Denise et al. Production of Botulinum Toxin A, 2013, p. 1-24.*
Gessler et al. FEMS Immunology and Medical Microbiology, 1999, 24:361-367.*
Binz, T., et al., "The Complete Sequence of Botulinum Neurotoxin Type A and Comparision with Other Clostridial Neurotoxins", "The Journal of Biological Chemistry", Jun. 5, 1990, pp. 9153-9158, vol. 265, No. 16.
Oguma, K., et al., "Structure and Function of Clostridium Botulinum Progenitor Toxin", "J. Toxicology—Toxin Reviews", 1999, pp. 17-34, vol. 18, No. 1.
Park, M.K., et al., "Binding of Clostridium botulinum type B toxin to rat brain synaptosome", "FEMS Microbiology Letters", Jun. 18, 1990, pp. 243-248, vol. 72.
Poulain, B., et al., "Neurotransmitter release is blocked intracellularly by botulinum neurotoxin, and this requires uptake of both toxin polypeptides by a process mediated by the larger chain", "Proceedings of the National Academy of Sciences", Jun. 1988, pp. 4090-4094, vol. 85.
Prusiner, S., "Creutzfeldt-Jakob Disease and Scrapie Prions", "Alzheimer Disease and Associated Disorders", 1989, pp. 52-78, vol. 3, No. 1/2.
Simpson, L., "Molecular Pharmacology of Botulinum Toxin and Tetanus Toxin", "Annual Review of Pharmacology and Toxicology", 1986, pp. 427-453, vol. 26.

(Continued)

*Primary Examiner* — Bin Shen
(74) *Attorney, Agent, or Firm* — Hultquist, PLLC; Steven J. Hultquist

(57) ABSTRACT

The present invention relates to a method for producing a botulinum toxin comprising: (a) treating a culture of a botulinum toxin-producing strain with acid to form a botulinum toxin-containing precipitate; (b) adding a buffer to the botulinum toxin-containing precipitate of step (a), followed by clarification by at least one method selected from the group consisting of depth filtration (DF), microfiltration (MF), ultrafiltration (UF), sterile filtration, membrane chromatography (MC) and centrifugation; (c) subjecting the botulinum toxin-containing solution of step (b) to UF diafiltration, ammonium sulfate precipitation or hydrochloric acid precipitation, and then diluting a retentate resulting from the UF diafiltration in a buffer or dissolving a precipitate resulting from the ammonium sulfate precipitation or hydrochloric acid precipitate in a buffer; and (d) subjecting the retentate dilution, ammonium sulfate precipitate solution or hydrochloric acid precipitate solution of step (c) to anion-exchange chromatography (AEX) to purify the botulinum toxin.

27 Claims, 4 Drawing Sheets
(3 of 4 Drawing Sheet(s) Filed in Color)

(56) References Cited

OTHER PUBLICATIONS

Simpson, L., et al, "Isolation and Characterization of the Botulinum Neurotoxins", "Methods in Enzymology", 1988, pp. 76-85, vol. 165.

Sugiyama, H., "Clostridium botulinum Neurotoxin", "Microbiological Reviews", Sep. 1980, pp. 419-448, vol. 44, No. 3.

Aptemehko, A., et al., "On the Absence of Interchangeability of Botulinum Toxin Type A Drugs", "Medical Advice", 2015, pp. 112-123, No. 5.

Aptemehko, A., et al., "On the Absence of Interchangeability of Botulinum Toxin Type A Drugs", "Medical Advice", 2015, Page(s) English Abstract, No. 5.

\* cited by examiner

FIG. 1

Conventional Production Method

Clostridium botulinum strain
↓
Culture
↓
Sulfuric acid precipitation/pH neutralization
↓
Enzymatic treatment and centrifugation (supernatant)
↓
HCl treatment
↓
Centrifugation (pellets)
↓
Re-dissolution of pellets
↓
Anion-exchange chromatography (AEX FT) purification
↓
Separation of 19S botulinum toxin

Production method according to the present invention

Clostridium botulinum strain
↓
Culture
↓
Sulfuric acid precipitation/pH neutralization
↓
Depth filtration, microfiltration, ultrafiltration, sterile filtration, membrane chromatography, or centrifugation
↓
UF diafiltration, ammonium sulfate precipitation or HCl precipitation
↓
Dilution of retentate or dissolution of precipitate
↓
Anion-exchange chromatography (AEX FT) purification
↓
Separation of 19S botulinum toxin
↓
Anion-exchange chromatography (AEX FT/Binding) purification
↓
Cation-exchange chromatography (CEX binding) purification
↓
Separation of 7S botulinum toxin

METHOD AND PRODUCING BOTULINUM TOXIN

CROSS-REFERENCE TO RELATED APPLICATIONS

This application is a U.S. national phase under the provisions of 35 U.S.C. § 371 of International Patent Application No. PCT/KR16/13506 filed Nov. 23, 2016, which in turn claims priority of Korean Patent Application No. 10-2015-0168196 filed Nov. 30, 2015. The disclosures of such international patent application and Korean priority patent application are hereby incorporated herein by reference in their respective entireties, for all purposes.

TECHNICAL FIELD

The present invention relates to a method for producing a botulinum toxin by an animal product-free (APF) process, and more particularly, to a method for producing a botulinum toxin, comprising the steps of: (a) treating a culture of a botulinum toxin-producing strain with acid to form a botulinum toxin-containing precipitate; (b) adding a buffer to the botulinum toxin-containing precipitate of step (a), and then clarifying by one or more method selected from the group consisting of depth filtration (DF), microfiltration (MF), ultrafiltration (UF), sterile filtration, membrane chromatography (MC) and centrifugation; (c) subjecting the botulinum toxin-containing solution of step (b) to UF diafiltration, ammonium sulfate precipitation or hydrochloric acid precipitation, and then diluting a retentate resulting from the UF diafiltration in a buffer or dissolving a precipitate resulting from the ammonium sulfate precipitation or hydrochloric acid precipitate in a buffer; and (d) subjecting the retentate dilution, ammonium sulfate precipitate solution or hydrochloric acid precipitate solution of step (c) to anion-exchange chromatography (AEX), thereby purifying the botulinum toxin.

BACKGROUND ART

A variety of *Clostridium* sp. strains that secrete neurotoxic toxins have been discovered since 1980's, and the characterization of toxins that are secreted from these strains has been made for the past 70 years.

Neurotoxic toxins derived from the *Clostridium* sp. strains, that is, botulinum toxins, are classified into eight types (types A to H) depending on their serological properties. Each of the toxins has a toxin protein having a size of about 150 kDa and naturally contains a complex of several non-toxic proteins bound thereto. A medium complex (300 kDa) is composed of a toxin protein and a non-toxic non-hemagglutinin protein, and a large complex (450 kDa) and a very large complex (900 kDa) are composed of the medium-sized complex bound to hemagglutinin (Sugiyama, H., *Microbiol. Rev.*, 44:419, 1980). Such non-toxic proteins are known to function to protect the toxin from low pH and various proteases in the intestines.

The toxin is synthesized as a single polypeptide having a molecular weight of about 150 kDa in cells, and then cleaved at a position of ⅓ starting from the N-terminal end by the action of intracellular protease or treatment with an artificial enzyme such as trypsin into two units: a light chain (L; molecular weight: 50 kDa) and a heavy chain (H; molecular weight: 100 kDa). The cleaved toxin has greatly increased toxicity compared to the single polypeptide. The two units are linked to each other by a disulfide bond and have different functions. The heavy chain binds to a receptor of a target cell (Park. M. K. et al., *FEMS Microbiol. Lett.*, 72:243, 1990) and functions to interact with a biomembrane at low pH (pH 4) to form a channel (Mantecucco, C. et al., *TIBS.*, 18:324, 1993), and the light chain has pharmacological activity, and thus imparts permeability to cells using a detergent or interferes with the secretion of a neurotransmitter when introduced into cells by, for example, electroporation (Poulain, B. et al., *Proc. Natl. Acad. Sci. USA.*, 85:4090, 1988).

The toxin inhibits the exocytosis of acetylcholine at the cholinergic presynapse of a neuromuscular junction to cause asthenia. It has been considered that even treatment with a very small amount of the toxin exhibits toxicity, suggesting that the toxin has any enzymatic activity (Simpson, L. L. et al., *Ann. Rev. Pharmaeol. Toxicol.*, 26:427, 1986).

According to a recent report, the toxin has metallopeptidase activity, and its substrates include composed of synaptobrevin, syntaxin, a synaptosomal associated protein of 25 KDa (SNAP25), etc., which are the unit proteins of an exocytosis machinery complex. Each type of toxin uses one of the above-described three proteins as its substrate, and it is known that type B, D, F and G toxins cleave synaptobrevin at a specific site, type A and E toxins cleave SNAP25 at a specific site, and type C cleaves syntaxin at a specific site (Binz, T. et al., *J. Biol. Chem.*, 265:9153, 1994).

Particularly, botulinum toxin type A is known to be soluble in a dilute aqueous solution at a pH of 4.0-6.8. It is known that a stable non-toxic protein is separated from neurotoxin at a pH of about 7 or higher, and as a result, the toxicity is gradually lost. Particularly, it is known that the toxicity decreases as pH and temperature increase.

The botulinum toxin is fatal to the human body even in small amounts and is easy to produce in large amounts. Thus, it constitutes four major bio-terror weapons together with *Bacillus anthracis, Yersinia pestis* and smallpox virus. However, it was found that, when botulinum toxin type A is injected at a dose that does not systematically affect the human body, it can paralyze local muscle in the injected site. Based on this characteristic, botulinum toxin type A can be used in a wide range of applications, including winkle removing agents, agents for treating spastic hemiplegia and cerebral palsy, etc. Thus, the demand for botulinum toxin type A has increased, and studies on methods of producing botulinum toxin so as to satisfy the demand have been actively conducted.

A current typical commercial product is BOTOX® (a purified neurotoxin complex of botulinum toxin type A) that is commercially available from Allergan, Inc., USA. A 100-unit vial of BOTOX® is composed of about 5 ng of a purified neurotoxin complex of botulinum toxin type A, 0.5 mg of human serum albumin and 0.9 mg of sodium chloride and is reconstituted using sterile saline without a preservative (injection of 0.9% sodium chloride). Other commercial products include Dysport® (a complex of *Clostridium botulinum* toxin type A and hemagglutinin, which has lactose and human serum albumin in a pharmaceutical composition containing botulinum toxin and is reconstituted using 0.9% sodium chloride before use) that is commercially available from Ipsen Ltd., UK and MyoBloc® (an injectable solution (a pH of about 5.6) comprising botulinum toxin type B, human serum albumin, sodium succinate and sodium chloride) that is commercially available from Solstice Neurosciences, Inc.

Conventional methods used to produce botulinum toxins include an acid precipitation method, a method of precipitation with salt, and a chromatographic method.

For example, Japanese Unexamined Patent Application Publication No. 1994-192296 discloses a method of producing a crystalline botulinum toxin type A by culturing *Clostridium botulinum* bacteria, followed by acid precipitation, extraction, addition of nuclease, and crystallization. Further, U.S. Pat. No. 5,696,077 discloses a method of producing a crystalline botulinum toxin type B by culturing *Clostridium botulinum* bacteria, followed by acid precipitation, extraction, ion exchange chromatography, gel filtration chromatography and crystallization.

Simpson et al. produced a botulinum toxin type A by purifying botulinum neurotoxin by gravity flow chromatography, followed by HPLC, capture using affinity resin, size exclusion chromatography, and ion (anion and cation) exchange chromatography including the use of two different ion exchange columns (Method in Enzymology, 165:76, 1988), and Wang et al. used precipitation and ion chromatography to purify a botulinum toxin type A (Dermatol Las Faci Cosm Surg., 2002:58, 2002).

Moreover, U.S. Pat. No. 6,818,409 discloses the use of ion exchange and lactose columns to purify a botulinum toxin, and U.S. Pat. No. 7,452,697 discloses a method of preparing a botulinum toxin type A by ion exchange chromatography and hydrophobic chromatography. Korean Patent Unexamined Patent Application Publication No. 2009-0091501 discloses a method of purifying a botulinum toxin by acid precipitation and anion exchange chromatography, and U.S. Patent Publication No. 2013-0156756 discloses a method of purifying a botulinum toxin by anion exchange chromatography and cation exchange chromatography.

However, the conventional methods have problems in that the use of anion exchange chromatography adversely affects the gel banding pattern of botulinum toxins (U.S. Pat. No. 7,452,697) and in that these conventional methods are difficult to apply commercially, due to a long purification time. In addition, because *Clostridium botulinum* that is a botulinum toxin-producing strain is an anaerobic bacterium, there is a problem in that fermentation of the bacterium should be performed in an anaerobic system, and thus it is difficult to produce botulinum toxins in large amounts. In addition, there is a problem in that the active ingredient botulinum toxin purified by the above-described purification method is not clearly separated and identified, and thus contains impurities. Additionally, the conventional methods for producing botulinum toxins have a problem in that a filtration or dialysis process is necessarily performed to purify a high-purity botulinum toxin, suggesting that the purification process is complex and difficult.

In addition, in conventional processes for producing botulinum toxin, enzymes such as DNase or RNase were used to remove nucleic acids such as DNA or RNA (see, e.g., Korean Patent No. 10-1339349, and a conventional method for producing botulinum toxin as shown in FIG. 1). However, because enzymes such as DNase or RNase are of animal origin, these enzymes have the potential to contain various disease-causing substances, particularly abnormal prion proteins of animal origin known to cause transmissible spongiform encephalopathy, and thus have problems in terms of safety.

Transmissible spongiform encephalopathy (TSE) is known as a neurodegenerative disorder causing serious degeneration of neurons, and examples thereof includes bovine spongiform encephalopathy (BSE), Scrapie, Creutzfeldt-Jakob disease (CJD), Gerstmann-Straussler-Scheinker syndrome, Kuru, transmissible mink encephalopathy, chronic wasting disease, feline spongiform encephalopathy, etc., which affect humans and animals. It was reported that BSE crosses the species barrier and affects even humans.

The agent that causes transmissible spongiform encephalopathy (TSE) has characteristics in that it has no immunogenicity and the incubation period is long. From histopathological analysis of BSE-affected bovine brain tissue, it can be seen that special spongiform vacuoles were formed in the brain due to damage to neurons and deposition of abnormal protein fibers.

The cause of TSE is an infectious protein known as the abnormal prion. Unlike general viruses that require nucleic acid, the abnormal prion is an infectious particle composed of protein alone without containing nucleic acid. Regarding TSE, it is known that, when an abnormal prion ($PrP^{sc}$) that is an infectious particle binds to a normal prion ($PrP^{c}$), it is converted to a pathogenic prion which is then accumulated in the brain (Prusiner SB, Alzheimer Dis Assoc Disord., 3:52-78, 1989).

Creutzfeldt-Jakob disease is a rare neurodegenerative disorder of human transmissible spongiform encephalopathy (TSE) where the transmissible agent is apparently an abnormal isoform of a prion protein. An individual with Creutzfeldt-Jacob disease can deteriorate from apparent perfect health to akinetic mutism within six months. Thus, a potential risk may exist of acquiring a prion mediated disease, such as Creutzfeldt-Jacob disease, from the administration of a pharmaceutical composition which contains a biologic, such as a botulinum toxin, obtained using animal-derived products. Thus, if a pharmaceutical composition is prepared using drug substance produced using animal-derived components, it can subject the patient to a potential risk of receiving various pathogens or infectious agents.

Thus, a method of producing botulinum toxin by an animal product-free (APF) process is urgently needed to solve safety problems such as transmissible spongiform encephalopathy infection caused by such animal-derived components worldwide.

Under such a technical background, the present inventors have made extensive efforts to develop a method capable of preventing the risk of exposure to prion-mediated disease (transmissible spongiform encephalopathy (TSE)) and increasing the purity of botulinum toxin, and as a result, have found that when a culture of a botulinum toxin-producing strain is treated with acid to form a botulinum toxin precipitate and the formed botulinum toxin precipitate is clarified using at least one technique selected from the group consisting of depth filtration (DF), microfiltration (MF), ultrafiltration (UF), sterile filtration, membrane chromatography (MC) and centrifugation, which are pretreatment processes, followed by performing a process selected from among UF diafiltration, ammonium sulfate precipitation and hydrochloric acid precipitation, followed by purification using anion/cation-exchange chromatography, an enzymatic treatment step that uses animal products can be omitted to eliminate the risk of causing prion-mediated disease, and the purity of the botulinum toxin can be increased, thereby completing the present invention.

DISCLOSURE OF INVENTION

Technical Problem

It is an object of the present invention to provide a more efficient and safe method for producing botulinum toxin, which can be performed under animal product-free (APF) conditions.

More specifically, an object of the present invention is to provide a method for producing botulinum toxin, in which an enzymatic treatment step using animal products (APs) is replaced by clarification of the botulinum toxin using at least one technique selected from the group consisting of depth filtration (DF), microfiltration (MF), ultrafiltration (UF), sterile filtration, membrane chromatography (MC) and centrifugation, which are pretreatment processes, followed by performing one process selected from among UF diafiltration, ammonium sulfate precipitation and hydrochloric acid precipitation, followed by further purification using anion/cation-exchange chromatography, thereby ensuring safety with very high yield.

Technical Solution

To achieve the above object, the present invention provides a method for producing a botulinum toxin, comprising the steps of:

(a) treating a culture of a botulinum toxin-producing strain with acid to form a botulinum toxin-containing precipitate;

(b) adding a buffer to the botulinum toxin-containing precipitate of step (a), and then clarifying by one or more method selected from the group consisting of depth filtration (DF), microfiltration (MF), ultrafiltration (UF), sterile filtration, membrane chromatography (MC) and centrifugation;

(c) subjecting the botulinum toxin-containing solution of step (b) to UF diafiltration, ammonium sulfate precipitation or hydrochloric acid precipitation, and then diluting a retentate resulting from the UF diafiltration in a buffer, or dissolving a precipitate resulting from the ammonium sulfate precipitation or hydrochloric acid precipitate in a buffer; and (d) subjecting the retentate dilution, ammonium sulfate precipitate solution or hydrochloric acid precipitate solution of step (c) to anion-exchange chromatography (AEX), thereby purifying the botulinum toxin.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a schematic diagram comparing a process for producing a botulinum toxin according to the present invention with a conventional process.

BEST MODE FOR CARRYING OUT THE INVENTION

Figure 2:
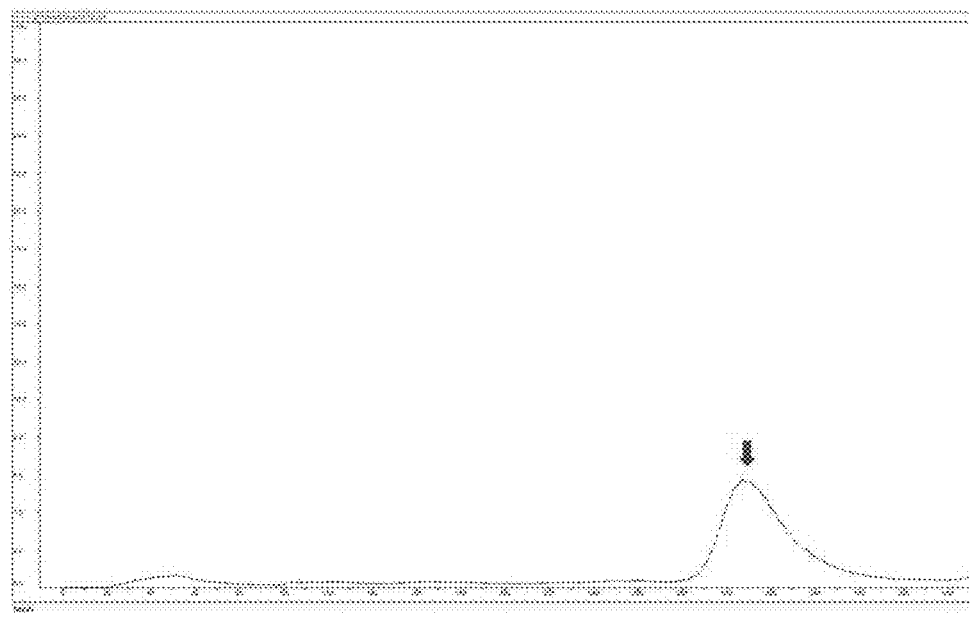
FIG. 2 shows a chromatogram of first anion-exchange chromatography purification (AEX) step and second anion-exchange chromatography purification (AEX) step for purifying a botulinum toxin.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In the present invention, in order to develop an APF (animal product-free) and low-molecular-weight botulinum toxin purification process, it was attempted to develop a process to replace the enzymatic treatment step of a conventional process, which uses animal products (APs). Thus, filtration using a depth filter, a conventional hydrochloric acid precipitation process, a process using ammonium sulfate and a process using a UF system were performed, and as a result, it was shown that the purity of the resulting botulinum toxin was higher than that of a botulinum toxin produced by the conventional method. This suggests that the use of the above-described method according to the present invention makes it possible to produce a high-purity botulinum toxin from a culture of a strain under TSE-free conditions in a safe manner.

The terms "process" and "separation", as used interchangeably herein, refer to the use of at least one method or system to achieve a specific purpose (for example, botulinum toxin purification) in a purification process.

In an example of the present invention, when clarification was performed by at least one method selected from the group consisting of depth filtration (DF), microfiltration (MF), ultrafiltration (UF), sterile filtration, membrane chromatography (MC) and centrifugation, followed by UF diafiltration, ammonium sulfate precipitation or acid precipitation, a botulinum toxin having satisfactory purity could be obtained even by an anion-exchange chromatography (AEX) process alone.

Therefore, in one aspect, the present invention is directed to a method for producing a botulinum toxin, and more particularly, to a method for producing a botulinum toxin, comprising the steps of:

(a) treating a culture of a botulinum toxin-producing strain with acid to form a botulinum toxin-containing precipitate;

(b) adding a buffer to the botulinum toxin-containing precipitate of step (a), and then clarifying by one or more method selected from the group consisting of depth filtration (DF), microfiltration (MF), ultrafiltration (UF), sterile filtration, membrane chromatography (MC) and centrifugation;

(c) subjecting the botulinum toxin-containing solution of step (b) to UF diafiltration, ammonium sulfate precipitation or hydrochloric acid precipitation, and then diluting a retentate resulting from the UF diafiltration in a buffer, or dissolving a precipitate resulting from the ammonium sulfate precipitation or hydrochloric acid precipitate in a buffer; and (d) subjecting the retentate dilution, ammonium sulfate precipitate solution or hydrochloric acid precipitate solution of step (c) to anion-exchange chromatography (AEX), thereby purifying the botulinum toxin.

The botulinum toxin purified according to the production method of the present invention may have a form of 7S or 19S (molecular weight: 150-900 kDa).

In the present invention, the botulinum toxin-producing strain is preferably *Clostridium botulinum* or a mutant strain thereof, but is not limited thereto, and it will be obvious to those skilled in the art that any strain capable of producing a botulinum toxin may be used.

As used herein, the term "botulinum toxin" is meant to include not only neurotoxins (NTXs) produced by the *Clostridium botulinum* strain or a mutant strain thereof, but also modified, recombinant, hybrid and chimeric botulinum toxins. A recombinant botulinum toxin may have a light chain and/or heavy chain produced by non-*Clostridium* species in a recombinant manner. In addition, the term "botulinum toxin" as used herein is meant to include botulinum toxin serotypes A, B, C, D, E, F and G, botulinum toxin complexes (i.e., 300, 600 and 900 kDa complexes), and a pure botulinum toxin (i.e., 150 kDa neurotoxic molecule), which are all useful in the practice of the present invention.

NTXs (7S) that are the main components of botulinum toxins are associated with nontoxic components in cultures or in foods, and become large complexes (Oguma et al., "Structure and function of *Clostridium botulinum* progenitor toxin.", J. Toxical-Toxin Reviews, 18:17-34, 1999). Type A strain that produces botulinum toxin serotype A produces three forms of progenitor toxins designated as LL (19S, 900 kDa), L (16S, 500 kDa) and M (12S, 300 kDa) toxins, all of which are considered to be fully activated, while type B, C, and D strains produce two forms, L and M. In addition, type E, F and G produce only a single form of toxin; types E and F produce M toxin, and type G produces L toxin. M toxin consists of a NTX (7S, 150 kDa) and a nontoxic component showing no hemagglutinin (HA) activity, which is described as non-toxic non-HA (NTNH).

As used herein, the term "produced botulinum toxin" means a pure botulinum toxin or a botulinum toxin complex, which is separated or substantially separated from other proteins or impurities that can be accompanied by the botulinum toxin when the botulinum toxin is collected from a culturing or fermentation process. Thus, the produced botulinum toxin has a purity of at least 90%, preferably at least 95%, and most preferably at least 98%. Particularly, the produced botulinum toxin in the present invention may be a botulinum toxin type A protein having a purity of at least 98%.

Culture of the *Clostridium botulinum* strain for producing the botulinum toxin can be performed using a conventional method known in the art and a conventional medium that may be used for culture.

By way of non-limiting example, a medium for culture of *Clostridium botulinum* strain may include a casein hydrolysate, a yeast extract, glucose and the like, and the culture is performed at a temperature of 25 to 40° C. for 90-180 hours, preferably 100-150 hours.

The acid precipitation of step (a) may be performed by adding acid, preferably sulfuric acid or hydrochloric acid, to a culture of the strain after culturing, so that the culture reaches a pH of 3.0-4.5, preferably 3.3-4.0, most preferably 3.4-3.6.

The acid precipitation of step (a) is based on the principle in which the addition of acid to a culture containing many kinds of proteins reduces the pH of the culture while killing botulinum bacteria remaining after culture so that the proteins reach the isoelectric point to precipitate. It includes crystallization in a broad sense, and the precipitation method is a method of roughly separating a desired material in a mixed state, unlike crystallization focused on purifying the desired material with high purity. In the precipitation method, impurities having a structure similar to the desired material are also precipitated. Herein, the pH is adjusted to about 3.0-4.5. The recovery rate of the botulinum toxin increases as the pH decreases. If the pH is 3.0 or lower, it will affect the botulinum toxin itself, and if the pH is 4.5 or higher, the recovery rate of the botulinum toxin will decrease. For these reasons, the pH is preferably within the above-specific range. Particularly, the pH is most preferably 3.4-3.6, because the recovery rate of the botulinum toxin is the highest in this pH range. When the pH of the botulinum strain culture reaches a suitable range after addition of acid, the acid is added to the culture until the change in the pH no longer appears, and then the culture is allowed to stand at room temperature for 10-30 hours, followed by removal of the supernatant.

In the present invention, the acid precipitation in step (a) may be performed once or more.

As used herein, the term "clarification" means re-dissolving a precipitate or the like in a buffer, and then removing impurities from the solution resulting from the re-dissolution. The "clarification" step in the present invention may generally be performed using one or more steps of including any of the following alone or various combinations thereof, for example, filtration, precipitation, flocculation and settling. More specifically, the clarification step may be performed using at least one technique selected from the group consisting of depth filtration (DF), microfiltration (MF), ultrafiltration (UF), sterile filtration, membrane chromatography (MC) and centrifugation. Through the clarification step in the present invention, impurities, particularly nucleic acid impurities, HCD, cell debris and endotoxin, contained in the re-dissolved toxin precipitate, may be removed.

In some embodiments, the present invention provides an improvement over the conventional clarification step commonly used in various purification schemes. The clarification step generally involves the removal of one or more undesirable entities and is typically performed prior to a step involving capture of the desired target molecule. Another aspect of clarification is the removal of soluble and insoluble components in a sample which may later result in the fouling of a sterile filter in a purification process, thereby making the overall purification process more economical. Furthermore, methods for enhancing clarification efficiency, for example, precipitation can be used. Precipitation of impurities can be performed by various methods such as flocculation, pH adjustment (acid precipitation), temperature shifts, phase change due to using stimulus-responsive polymers or small molecules, or any combinations of these methods.

As used herein, the term "depth filtration (DF)" means removing particles (e.g., impurities) from a solution using a series of filters with decreasing pore size. The term "depth filter" as used herein achieves filtration within the depth of the filter material. Such filters are those that comprise a random matrix of fibers bonded to form a complex, tortuous maze of flow channels. Particle separation in these filters results from entrapment by or adsorption to, the fiber matrix. The most frequently used depth filter media for bioprocessing of cell culture broths and other feedstocks consist of cellulose fibers, a filter aid such as DE, and a positively charged resin binder. Depth filter media, unlike absolute filters, retain particles throughout the porous media allowing for retention of particles both larger and smaller than the pore size. Particle retention is thought to involve both size exclusion and adsorption through hydrophobic, ionic and other interactions. Commercially available depth filters include Millistak+ Pod depth filter system, XOHC media (Millipore Corporation), Zeta Plus™ Depth Filter (3M Purification Inc.), etc. In the present invention, depth filtration may be performed using two or more depth filters arranged in parallel. In this case, commercially available depth filters may include Millistak+ mini DOHC (Millipore Corporation) and XOHC filters (Millipore Corporation).

In the present invention, the depth filter generally has a nominal pore size of 0.01-20 μm, preferably 0.1-8-82 m, is used for removal of flocculated cell debris and colloidal particulates having a size larger than the above pore size and cellular biomass including particulates smaller than the above pore size, and may include a porous depth filter media having porous layers of varying pore ratings.

Thus, when depth filtration is used in the present invention, it is easy to remove impurities (e.g., nucleic acids), cell debris, endotoxin, etc., from the botulinum toxin precipitate.

As used herein, the term "microfiltration (MF)" or "ultrafiltration (UF)" is a process that fractionates a target solute (e.g., botulinum toxin) through the pores of a membrane under a certain pressure according to the size and structure of the solute of a mixture solution. For example, clarification of a solution can be performed at a pressure of 5-40 psig and a temperature of 4 to 60° C. by use of a PS (polysulfone) membrane for 0.1 μm size or 750 kDa molecular weight cut-off (MWCO) separation.

Generally, microfiltration is a process which is carried out prior to ultrafiltration, and is used to separate particles having a size of 0.1-10 μm from a solution. It is generally used to separate a polymer having a molecular weight of $1 \times 10^5$ g/mol. In addition, microfiltration may be used to remove sediments, protozoan animals, large bacteria, etc. In the present invention, microfiltration may be easily used to remove polymers or cell debris. Generally, the microfiltration process is performed using a pressure pump or a vacuum pump at a velocity of 0.1-5 m/s, preferably 1-3 m/s, and a pressure of 50-600 kPa, preferably 100-400 kPa.

Ultrafiltration is used to separate particles having a size of 0.01-0.1 μm from a solution, and the particles generally correspond to polymers having a molecular weight of $1 \times 10^3 - 1 \times 10^5$ Da. Ultrafiltration is used to remove proteins, endotoxin, virus, silica, etc. In the present invention, when an ultrafiltration membrane for 100-300 kDa MWCO is used, it can remove impurities from the botulinum toxin precipitate and concentrate the botulinum toxin.

As used herein, "sterile filtration" is a process that uses a microfilter or a membrane filter, can replace heating, irradiation or chemical treatment, and can safely clarify solutions containing target substances (e.g., biologics, botulinum toxins, etc.). For removal of microorganisms that can be contained in solutions, a microfilter having a pore size of 0.1-0.3 μm, preferably 0.15-0.25 μm, most preferably 0.2-0.22 μm, is used, and for removal and inactivation of virus, a nanofilter having a pore size of 20-50 nm is used. In addition, for removal of microorganisms, virus, etc., a clarification process may also be performed using a membrane filter which has a specific pore size and which is made of cellulose ester or PES (polyethersulfone).

In the present invention, "membrane chromatography (MC)" may be used as a process for separation of a target substance (e.g., botulinum toxin), which is contrasted with "resin chromatography". Resin chromatography generally uses a spherical porous resin and is based on diffusion greater than convection of solution, whereas membrane chromatography uses a planar macroporous membrane and is based on convection greater than diffusion of solution. Thus, in membrane chromatography, the separation efficiency of solution is relatively high, and thus the access of viruses, plasmids, large protein complexes, etc., to the membrane, is easy, thereby making separation easy. Commercially available membrane chromatography may include Mustang Q membrane chromatography capsule (Pall Corporation), Sartobind Q (Sartorius Stedim Biotech GmbH), but is not limited thereto.

In the present invention, centrifugation may preferably be performed at a centrifugal force of preferably at 12,000~15,000 g.

In the present invention, the botulinum toxin clarification of step (b) comprises a step of dissolving the toxin precipitate resulting from step (a) by addition of phosphate buffer, preferably sodium phosphate buffer, and clarifying the precipitate. Herein, the pH of the phosphate buffer is about 3.0-8.0, preferably about 4.0-7.0, and the solution is adjusted to the final pH of 4.5-6.5, preferably 5.5-6.2, more preferably 4.8-5.8. In this pH range, clarification of the toxin may be performed.

In the present invention, dilution or dissolution of the botulinum toxin in step (c) comprises a step of adding phosphate buffer, preferably sodium phosphate buffer, to the toxin resulting from step (b) to dilute the retentate or dissolve the precipitate. Herein, the pH of the phosphate buffer is preferably about 4.0-8.5, and a base may be added to adjust the final pH to 4.5-8, preferably 5.5-7.5, more preferably 6-7. In this pH range, dilution or dissolution of the toxin may be performed.

In the present invention, depth filtration (DF) of the botulinum toxin in step (b) may be performed using a peristaltic pump, and UF diafiltration, ammonium sulfate precipitation or hydrochloric acid precipitation in step (c) may be performed once or more.

As used herein, the term "UF diafiltration" means performing diafiltration using the above-described ultrafiltration (UF), but is not limited thereto. "Diafiltration" means a technique that removes or collects any component (e.g., particles) from a target substance (solution) using a permeable filter capable of achieving separation according to the molecular weight (molecular size) of the component, thereby increasing the purity of the target substance.

The step of precipitation with ammonium sulfate corresponds to a salting out process in which a salt (ammonium sulfate, etc.) that easily dissolves in water is added to a protein mixture to increase the ionic strength to thereby to form a protein precipitate. If a desired protein precipitates mainly upon saturation with 30% (w/v) ammonium sulfate, the desired protein can be precipitated by precipitating out proteins other than the desired protein at a ammonium sulfate saturation concentration of 30% (w/v) or lower, and then adding ammonium sulfate to a saturation concentration of 30% (w/v), and can be collected by centrifugation. The salting out operation is frequently used as initial means for purification. The ammonium sulfate solution used may have an ammonium sulfate concentration of 10-50% (w/v), preferably 20-40% (w/v). In addition, hydrochloric acid precipitation in step (c) may be performed by adding hydrochloric acid to reach a pH of 2-5, preferably 2.5-4.5.

The anion-exchange chromatography in step (d) may be performed at a pH of 2-9, preferably 3-8, and a conductivity of 2-40 mS/cm, preferably 3-30 mS/cm. In step (d), botulinum toxin may be collected as a botulinum toxin-containing fraction (flow-through mode) of a flow-through (FT) fraction eluted from anion-exchange chromatography or as a fraction containing the botulinum toxin bound to anion exchange chromatography resin. The finally purified botulinum toxin may have a form of 7S or 19S.

The term "FT (flow-through)", "flow-through process" or "flow-through purification", as used interchangeably herein, means a separation process in which at least one target molecule (e.g., botulinum toxin) contained in a biopharmaceutical formulation together with one or more impurities passes through a material and one or more impurities generally bind to the material and the target molecule generally does not bind to the material (that is, flows through the materials).

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho/cm (mS/cm), and can be measured using a conductivity meter, such as various models of Orion conductivity meters. Because electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers may be modified to achieve the desired conductivity.

In the present invention, a column buffer that is used for the anion-exchange chromatography in step (d) may be sodium phosphate buffer, citrate buffer or Tris-HCl buffer, but is not limited thereto. The concentration of the column buffer is adjusted to 15-70 mM, preferably about 20-60 mM. The pH of the column buffer is adjusted to 2-9, preferably 3-8, and the flow rate of the mobile phase is controlled to 0.5-5.0 mL/min, preferably 1.0-3.0 mL/min. Herein, the conductivity of the buffer is adjusted to 2-40 mS/cm, preferably 3-30 mS/cm, and the sample is loaded into a column after completion of equilibration of the column.

In addition, in the present invention, it could be seen that, when the pH of the botulinum toxin-containing anion exchange chromatography fraction obtained through steps (a) to (d) was adjusted upward and when anion-exchange chromatography was performed again, followed by cation-exchange chromatography (CEX), a botulinum toxin having a very high purity, particularly a pure botulinum neurotoxin could be obtained.

Therefore, in another aspect, the present invention provides a method for producing a botulinum toxin, further comprising, after step (d), the steps of:

(e) adjusting the pH of the botulinum toxin-containing anion exchange chromatography fraction upward;

(f) purifying the pH-adjusted anion exchange chromatography fraction resulting from step (e) by anion exchange chromatography; and (h) purifying the diluted botulinum toxin resulting from step (f) using cation exchange chromatography (CEX).

Preferably, the method may further comprise, between step (f) and step (h), step (g) of adding a buffer to the purified anion exchange chromatography fraction to dilute the botulinum toxin.

In the present invention, when steps (e) to (h) are additionally performed, the anion-exchange chromatography (AEX) process in step (d) is referred to as "first anion-exchange chromatography process" for convenience of explanation, and the AEX process in step (f) is referred to as "second anion-exchange chromatography process". Unless specified otherwise, the AEX process in step (d) refers to first anion-exchange chromatography in step (d). In addition, unless specified otherwise, TQ in the examples and the like means the first anion-exchange chromatography process, HQ means the second anion-exchange chromatography process, and XS means the cation-exchange chromatography process.

In the present invention, the "pH" of a solution means the acidity or alkalinity relative to the ionization of a water sample. The pH of water is neutral, i.e., 7. Most pH readings range from 0 to 14. Solutions with a higher [H+] than water (pH less than 7) are acidic; solutions with a lower [H+] than water (pH greater than 7) are basic or alkaline. pH can be measured using a pH meter. Buffer pH may be adjusted using an acid or base such as HCl or NaOH.

In the present invention, the upward adjustment of the pH of the anion-exchange chromatography fraction in step (e) may be performed once or more, and the upward adjustment of the pH in step (e) may be performed using at least one technique selected from the group consisting of UF diafiltration, pH titration, dialysis, and buffer exchange column chromatography. Preferably, upward adjustment of pH of the anion-exchange chromatography fraction in step (e) is performed using Tris-HCl buffer. Herein, the Tris-HCl buffer has a pH of 7.0-8.5, preferably 7.3-8.3. Thus, the pH may be adjusted to 7.0~8.5, preferable 7.3~8.3, more preferable 7.7~7.9.

The second anion-exchange chromatography in step (f) may be performed at a pH of 2-9, preferably 3-8, and a conductivity of 2-40 mS/cm, preferably 3-30 mS/cm. In step (f), a botulinum toxin maybe collected as a botulinum toxin-containing fraction (flow-through mode) of a flow-through (FT) fraction eluted from anion-exchange chromatography or may be collected as a fraction containing the botulinum toxin bound to anion exchange chromatography resin.

In the present invention, the buffer in step (g) is preferably a sodium phosphate buffer and has a pH of 6-8, preferably 6.5-7.5.

In the present invention, the cation-exchange chromatography in step (h) may be performed at a pH of 2-9, preferably 3-8. In the cation-exchange chromatography of step (h), the botulinum toxin may be collected as a fraction containing the botulinum toxin bound to the cation-exchange chromatography resin, and the finally purified botulinum toxin may have a form of 7S (molecular weight: 150 kDa).

In the method for producing the botulinum toxin according to the present invention, the resin that is used in the anion-exchange chromatography process includes diethylaminoethyl (DEAE), quaternary aminoethyl (QAE) and quaternary amine (Q) groups, but is not limited thereto. Preferably, TQ650, HQ, XQ, etc., may be used.

In the method for producing the botulinum toxin according to the present invention, the resin that is used in the cation-exchange chromatography process preferably includes carboxymethyl (CM), sulfoethyl (SE), sulfopropyl (SP), phosphate (P), and sulfonate (S), but is not limited thereto. More preferably, HS, XS, etc., may be used.

Cellulose ion exchange resin, for example, DE23™, DE32™, DE52™, CM-23™, CM-32™, and CM-52™ are available from a manufacturer (GE Healthcare, Lindesnes, Norway), and SEPHADEX-based and cross-linked ion exchangers are also known. For example, DEAE-, QAE-, CM-, SP-SEPHADEX and DEAE-, Q-, CM- and S-SEPHAROSE and SEPHAROSE Fast Flow are all available from a manufacturer (GE Healthcare Bio-Sciences). In addition, both DEAE and CM derivatized ethylene glycol-methacrylate copolymers (for example, TOYOPEARL™ DEAE-650S or M and TOYOPEARL™ CM-650S or M) are available from a manufacturer (Tosoh Bioscience LLC, King of Prussia, Pa.).

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Culture of *Clostridium Botulinum* Strain

A medium for culture of the *Clostridium botulinum* strain for producing a botulinum toxin had a composition comprising 2% casein hydrolysate, 1% yeast extract, 1% glucose and 0.5% thioglycollate, and sterilized at 121° C. for 30 minutes. Then, 20 μL of *Clostridium botulinum* (the Korean Centers for Disease Control and Prevention Accession No.: 4-029-CBB-IS-001) was inoculated into a culture tube containing 10 ml of the medium, and was subjected to primary seed culture (stationary culture) at 35° C. for 22-30 hours under anaerobic conditions. When the growth of the strain in the primary seed culture process was confirmed, 8 mL of the primary seed culture was inoculated into a culture bottle containing 800 ml of a sterile medium having the same medium composition and was subjected to secondary seed culture (stationary culture) at 35° C. for 8-15 hours under anaerobic conditions. When the growth of the strain in the secondary seed culture process was confirmed, 800 mL of the secondary seed culture was inoculated into a 10 L culture bottle containing 10 L of a sterile medium having the same sterilized medium composition and subjected to culture at 35° C. for 4-6 days under anaerobic conditions.

Example 2: Production of Botulinum Toxin 2-1: Sulfuric Acid Precipitation and pH Neutralization The step of precipitation with sulfuric acid is a protein separation process in which sulfuric acid is added to a culture containing many kinds of proteins to reduce the pH of the culture while killing botulinum bacteria remaining after culture so that the proteins reach the isoelectric point to precipitate. The main culture was performed as described in Example 1, and after completion of the main culture, the culture was collected in a 10 L culture container (10 L SUS pot). Then, 5N sulfuric acid was added to the culture so as to reach a pH of 3.4-3.6, and the culture was allowed to stand at room temperature for 12-20 hours so that it would be separated into a supernatant and a precipitate. The supernatant was removed, and 2.5-3.0 L of the sulfuric acid precipitate finally remained. pH neutralization (e.g. by pH titration) of the sulfuric acid precipitate remaining after removal of the supernatant was performed in the following manner. 700 mL of 1 M sodium phosphate (pH 5.3) was added to the sulfuric acid precipitate, followed by stirring. 5N NaOH was added to adjust the pH of the sulfuric acid precipitate to 5.9-6.1. The pH-neutralized sulfuric acid precipitate was collected.

2-2: Pretreatment Process

1) Conventional Process

The sulfuric acid precipitates resulting from Example 2-1 was treated according to a conventional process. Specifically, to remove DNA and RNA remaining in the precipitate, 60 mL of 0.4M benzamidine HCl, 100 mg of DNase and 300 mg of RNase were added, and to extract the botulinum toxin, the precipitate solution was incubated for about 3-7 hours. Then, the incubated precipitate solution was centrifuged at 4° C. and 12,000×g for 15 minutes, followed by collection of the supernatant. The pH of the supernatant was lowered to 3.4-3.6 by addition of 1N hydrochloric acid, and then the supernatant was allowed to stand at a temperature of 3 to 5° C. for 12-20 hours, thereby performing the process of precipitation with hydrochloric acid. The hydrochloric acid precipitate formed by the above-described process was centrifuged at 4° C. and 12000×g for 15 minutes to remove the supernatant, and the remaining toxin pellets were dissolved in 30 mL of sodium phosphate buffer (pH 6.5).

2) Depth Filtration Process

The sulfuric acid precipitates resulting from Example 2-1 as filtered using Zeta Plusm Encapsulated Capsule depth filter effective filtration (3M, BC0025S6OSPO5A) connected to a peristaltic pump.

i) UF Following Depth Filtration

The depth filtrate was subjected 10 times to diafiltration with 50 mM sodium phosphate (pH 6.5) using a UF system (PALL, TFF cassette 30 kDa), and then adjusted to a final volume of 30 mL.

ii) Ammonium Sulfate Precipitation Following Depth Filtration

Ammonium sulfate was added to the depth filtrate to a concentration of 30% (w/v), and then the filtrate was allowed to stand at a temperature of 3 to 5° C. for 12-20 hours. Then, the solution was centrifuged at 4° C. and 12,000×g for 15 minutes to remove the supernatant, and then the centrifuged pellets were re-dissolved in 30 mL of 50 mM sodium phosphate (pH 6.5).

iii) Hydrochloric Acid Precipitation Following Depth Filtration

1N HCl was added to the depth filtrate to lower the pH of the filtrate to 3.4-3.6, and then the solution was allowed to stand at a temperature of 3 to 5° C. for 12-20 hours. Next, the solution was centrifuged at 4° C. and 12,000×g for 15 minutes to remove the supernatant, and the centrifuged pellets were re-dissolved in 30 mL of 50 mM sodium phosphate (pH 6.5).

2-3: Purification Process

Measurement of the purity of the botulinum toxin purified by the TQ process (first anion-exchange chromatography process) was performed by a SEC (size exclusion chromatography) method using HPLC (Waters e2695). Herein, the mobile phase used was 100 mM sodium phosphate (pH 6.5), and a TSKgel G4000SWx1 (Tosoh Bioscience, P/N 08542) column was connected to a guard column (Tosoh Bioscience, P/N 08543), and 20 μg of the botulinum toxin protein was loaded into the column and allowed to flow at a rate of 1 mL/min for 30 minutes.

In order to visually examine the mixed state/purity/content of the botulinum toxin contained in the sample collected in each purification (process) step for the botulinum toxin purified by the TQ process (first anion-exchange chromatography process), the HQ process (second anion-exchange chromatography process) and the XS process (cation-exchange chromatography process), protein electrophoresis (SDS-PAGE) was performed. Specifically, the samples considered to contain the botulinum toxin were quantified by the Bradford method, and then a certain amount (e.g., 40 µg protein) of each sample was taken and suitably heated and/or dissolved, and 4-12% SDS-PAGE was performed using the denatured protein. The electrophoresed gel was stained with a suitable dye (silver nitrate or Coomassie Blue), and then the purity of the botulinum toxin in each purification step was visually examined.

2-3-1: TQ Purification (Anion Exchange Chromatography Flow-Through (AEX FT))

After completion of the pretreatment process of Example 2-2, in order to remove most major impurities other than the botulinum toxin, chromatography was performed in the following manner using ion-exchange resin.

(1) TQ resin was packed into an XK 26/40 column to a height of 30-34 cm, and then the column was mounted in AKTA Prime Plus.

(2) The column was equilibrated with equilibrium/elution buffer (50 mM sodium phosphate (pH 6.4-6.6, and 10±5 mS/cm)).

(3) 10 mL of the sample pretreated by the conventional process of Example 2-2 was loaded into the column and allowed to flow at a rate of 2 mL/min. After completion of the injection, 160-180 mL of equilibrium/elution buffer was loaded, and fractions were sequentially collected until the peak at a UV wavelength of 280 nm decreased to the baseline (the fractions were analyzed by SDS-PAGE).

(4) For regeneration of the column after collection of the fractions, 200 mL or more of washing buffer (50 mM sodium phosphate, pH 6.46.6, 1M NaCl) was loaded at a flow rate of 5 mL/min to wash the column.

(5) According to the procedures of (2) to (4) above, TQ purification was performed using the samples pretreated by other three methods (UF following depth filtration, ammonium sulfate precipitation following depth filtration, and hydrochloric acid precipitation following depth filtration) instead of the sample pretreated by the conventional process. Herein, for purification of a high-purity botulinum toxin, pH was maintained at 6.4-6.6, and conductivity was maintained at 10±5 mS/cm.

As a result, it was shown that the botulinum toxin was not adsorbed onto the TQ resin, and most major impurities were removed by adsorption, and thus a botulinum toxin could be produced with high purity. In addition, the resulting botulinum toxin had a form of 19S (molecular weight: about 900 kDa).

2-3-2: HQ Purification (Anion Exchange Chromatography: AEX, Biding Mode)

After completion of TQ purification, in order to further purify the botulinum toxin, chromatography using HQ ion-exchange resin (hereinafter referred to as "HQ process") was performed. In the HQ process, the sample resulting from TQ purification was purified in binding or FT (flow-through) mode. As used herein, the term "HQ (binding)" refers to a process that separates (or elutes) a target substance (e.g., botulinum toxin) based on the difference in quantity of electric charge of HQ resin capable of binding to the target substance, and the term "HQ (FT)" refers to a process in which, based on the difference in quantity of electric charge of HQ resin capable of binding to impurities which can mixed with a target substance (e.g., botulinum toxin), the target substance that flows through (FT) the HQ resin without binding to the HQ resin is separated from a sample.

HQ (Binding) Purification (AEX, Biding Mode)

(1) The sample, purified by TQ after pretreatment according to the conventional process, was subjected 10 times to diafiltration with 25 mM Tris-HCl buffer (pH 7.7-7.9) using a UF system (PALL, TFF cassette 30 kDa MWCO). The final pH of the sample was 7.7-7.9, and the volume was adjusted to 30 mL.

(2) HQ resin was packed in AKTA Prime Plus.

(3) The column was equilibrated with 25 mM Tris-HCl buffer (pH 7.7-7.9).

(4) The sample prepared in (1) was loaded into the equilibrated column at a flow rate of 2.5 mL/min, and washed with 40 mL of 25 mM Tris-HCl buffer (pH 7.7-7.9), and then eluted at 20 CV and 10% gradient. Fractions corresponding to the first peak were sequentially collected (the fractions were analyzed by SDS-PAGE).

(5) For regeneration of the column after collection of the fractions, 120 mL or more of washing buffer (25 mM Tris-HCl, pH 7.7-7.9, 1M NaCl) was loaded at a flow rate of 2.5 mL/min to wash the column.

(6) The procedures of (1) to (5) above were performed using the samples purified by TQ after treatment according to other three methods (TQ purification after UF following depth filtration, ammonium sulfate precipitation following depth filtration, and hydrochloric acid precipitation following depth filtration), instead of the sample purified by TQ after pretreatment according to the conventional method.

Figure 3:
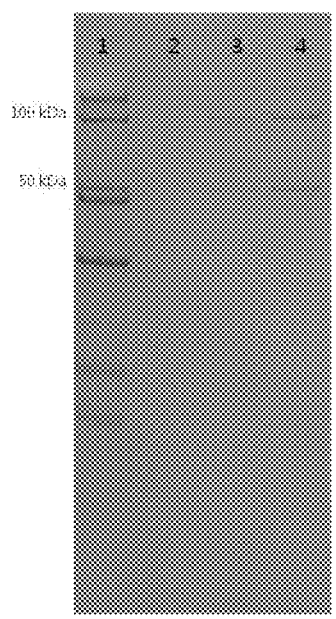
FIG. 3 shows the results of analyzing the purity of a botulinum toxin by SDS-PAGE after first anion-exchange chromatography purification (AEX) step and second anion-exchange chromatography purification (AEX) step.

As a result, it was shown that the botulinum toxin could be produced with high purity and that the resulting botulinum toxin had a form of 7S (molecular weight: about 150 kDa) (FIGS. 2 and 3).

2-3-3: HQ Purification (AEX, Biding Mode) and XS Purification (Binding Mode)

After completion of the HQ purification according to Example 2-3-2, in order to further purify the botulinum toxin, XS cation-exchange chromatography (CEX, binding mode) was further performed.

Specifically, the XS process was performed in the following manner.

(1) The sample, purified by HQ after pretreatment according to the conventional process of Example 2-2, was diluted to 1/4 using 50 mM sodium phosphate buffer (pH 6.9-7.1).

(2) XS resin was packed in AKTA Prime Plus.

(3) The column was equilibrated with equilibrium/elution buffer (50 mM sodium phosphate, pH 6.9-7.1).

(4) The diluted and HQ-purified sample of (1) was loaded into the equilibrated column at a flow rate of 1.6 mL/min, and washed with 50 mL of 50 mM sodium phosphate buffer (pH 6.9-7.1). And then, the sample was eluted at 20 CV and 12% gradient. Fractions corresponding to the first peak were sequentially collected (the fractions were analyzed by SDS-PAGE).

(5) For regeneration of the column after collection of the fractions, 20 mL or more of washing buffer (50 mM sodium phosphate, pH 6.9-7.1, 1M NaCl) was loaded at a flow rate of 1.6 mL/min to wash the column.

(6) The procedures of (1) to (5) above were performed using the samples purified by TQ and HQ after treatment according to other three methods (TQ purification after UF following depth filtration, ammonium sulfate precipitation following depth filtration, and hydrochloric acid precipitation following depth filtration), instead of the sample purified by HQ after pretreatment according to the conventional method.

Figure 4:
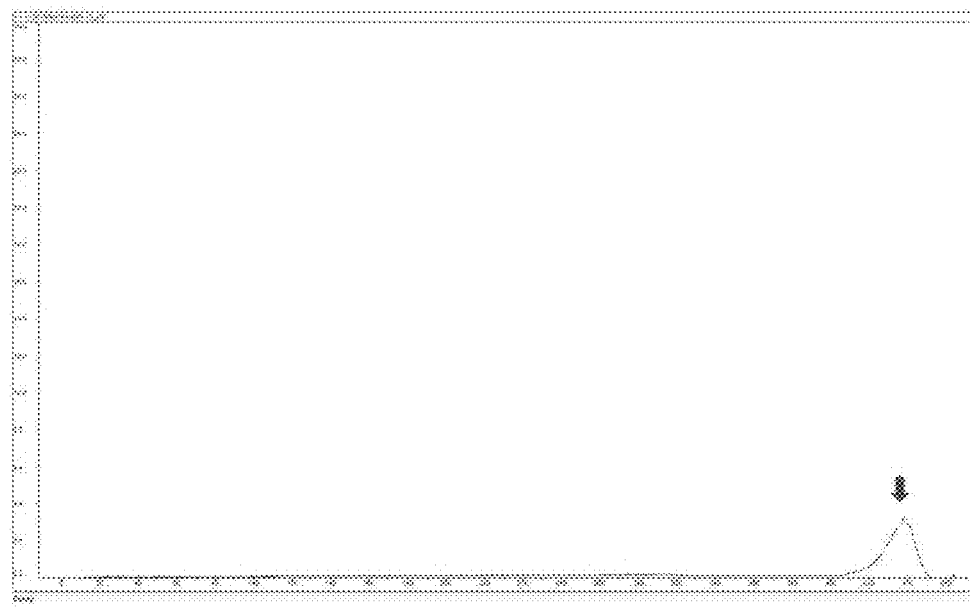
FIG. 4 shows a chromatogram of first anion-exchange chromatography purification (AEX), second anion-exchange chromatography purification (AEX, binding mode) and cation-exchange chromatography (CEX) steps for a botulinum toxin.
Figure 5:
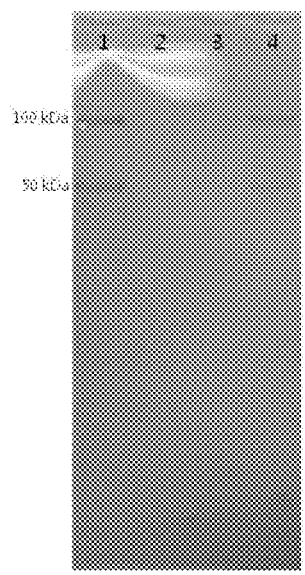
FIG. 5 shows the results of analyzing the purity of a botulinum toxin by SDS-PAGE after first anion-exchange chromatography purification (AEX), second anion-exchange chromatography purification (AEX, binding mode) and cation-exchange chromatography (CEX) steps.

As a result, it was shown that the botulinum toxin could be produced with high purity and that the final botulinum toxin had a form of 7S (molecular weight: about 150 kDa) (FIGS. 4 and 5).

2-3-4: HQ Purification (AEX, FT Mode) and XS Purification (Binding Mode)

According to the botulinum toxin production method described in Example 2-3-3 above, a botulinum toxin was produced using the flow-through mode instead of the binding mode in the HQ (AEX) purification process.

HQ (AEX, FT Mode) Process

HQ purification (AEX, FT mode) was performed in the following manner.

The sample, purified by TQ after pretreatment according to the conventional process, was subjected 10 times to diafiltration with 25 mM Tris-HCl buffer (pH 7.7-7.9, conductivity 7.0-7.5 mS/cm) using a UF system (PALL, TFF cassette 30 kDa MWCO). The final pH of the sample was 7.7-7.9, and the volume of the sample was adjusted to 30 mL. Next, the sample was subjected to a HQ (FT mode) process.

(1) HQ resin was packed in AKTA Prime Plus.

(2) The column was equilibrated with 25 mM Tris-HCl buffer (pH 7.7-7.9, conductivity: 7.0-7.5 mS/cm).

(3) The TQ-purified sample was loaded at a flow rate of 1.5 mL/min, and eluted with 40 mL of 25 mM Tris-HCl buffer (pH 7.7-7.9, conductivity: 7.0-7.5 mS/cm). Fractions corresponding to the peak were collected (the fractions were analyzed by SDS-PAGE).

(4) For regeneration of the column after collection of the fractions, 40 mL or more of washing buffer (25 mM Tris-HCl, pH 7.7-7.9, 1M NaCl) was loaded at a flow rate of 1.5 mL/min to wash the column.

XS Process using HQ (FT) Sample

In order to increase the purity of the botulinum toxin, the sample purified by the HQ (FT) process was further purified by an XS (binding) process.

(1) The sample purified by the HQ (FT) process was diluted to ¼ using 50 mM sodium phosphate buffer (pH 6.9-7.1).

(2) XS resin was loaded in AKTA Prime Plus.

(3) The column was equilibrated with 50 mM sodium phosphate buffer (pH 6.9-7.1).

(4) The HQ-purified sample diluted in (1) above, was loaded into the column at a flow rate of 1.5 mL/min, and washed with 50 mL of 50 mM sodium phosphate buffer (pH 6.9-7.1). And then, the sample was eluted at 60 CV and 12% gradient. Fractions corresponding to the first peak were collected (the fractions were analyzed by SDS-PAGE).

(5) For regeneration of the column after collection of the fractions, 20 mL or more of washing buffer (50 mM sodium phosphate, pH 6.9-7.1, 1M NaCl) was loaded at a flow rate of 1.5 mL/min to wash the column.

Figure 6:
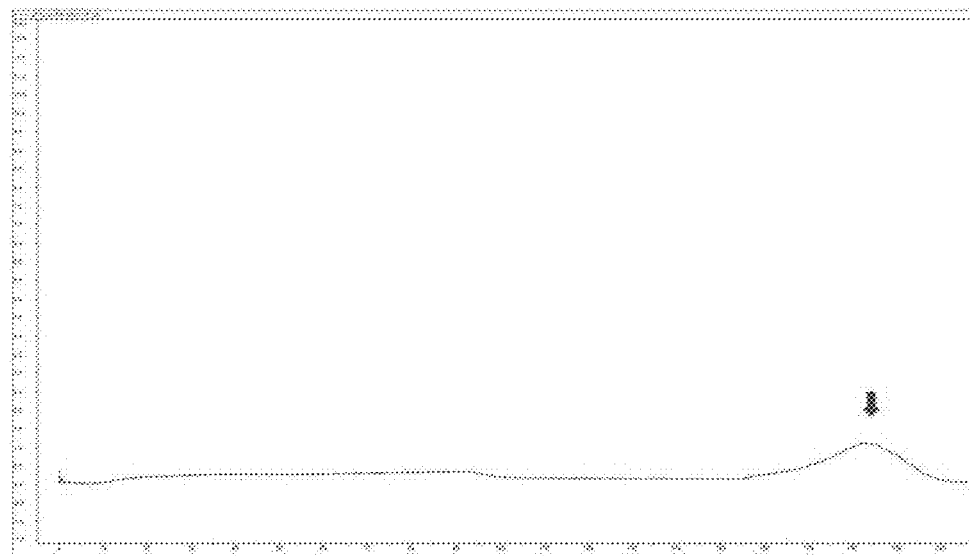
FIG. 6 shows a chromatogram of first anion-exchange chromatography purification (AEX), second anion-exchange chromatography purification (AEX, flow through mode) and cation-exchange chromatography (CEX) steps for a botulinum toxin.
Figure 7:
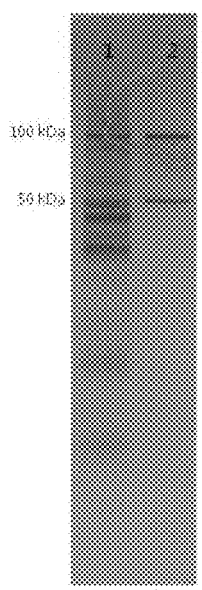
FIG. 7 shows the results of analyzing the purity of a botulinum toxin by SDS-PAGE after first anion-exchange chromatography purification (AEX), second anion-exchange chromatography purification (AEX, flow through mode) and cation-exchange chromatography (CEX) steps.

As a result, as shown in FIGS. 6 and 7, it was found that the botulinum toxin in the form of 7S (molecular weight: about 150 kDa) could be produced with a purity of 98% or higher.

Taken together, as shown in FIGS. 2 to 7, in the botulinum toxin-containing sample obtained by anion-exchange chromatography (TQ (binding or FT mode) purification) after performing either the conventional process of Example 2 or the hydrochloric acid precipitation process following depth filtration, impurities other than 138 kDa (NTNH), 98 kDa (heavy chain), 52 kDa (light chain), 50 kDa (HA), 33 kDa (HA), 20 kDa (HA) and 17 kDa (HA), which are naturally observed in toxin 19S, were observed in the smallest amount.

Furthermore, in the botulinum toxin-containing sample obtained by anion-exchange chromatography (TQ (binding or FT mode) purification) after UF diafiltration following depth filtration, an impurity protein band of about 13 kDa was observed.

In addition, in the botulinum toxin-containing sample obtained by anion-exchange chromatography (TQ (binding or FT mode) purification) after ammonium sulfate precipitation following depth filtration, an impurity protein band of about 37 kDa was observed.

However, as can be seen from the results of HQ and XS purification processes after dissociation of toxin complex for purification of the low-molecular-weight botulinum toxin, no impurity protein band was observed in all the botulinum toxin-containing samples regardless of the kind of four pretreatment processes (the conventional process, UF following depth filtration, ammonium sulfate precipitation following depth filtration, and hydrochloric acid precipitation following depth filtration), and only low-molecular-weight botulinum toxins with 98 kDa (heavy chain) and 52 kDa (light chain) were observed.

Particularly, the most efficient process capable of replacing enzymatic treatment and extraction processes for botulinum toxin-containing samples in order to separate botulinum toxin 19S is anion-exchange chromatography purification (TQ (binding or FT mode) performed after each of sulfuric acid precipitation, depth filtration and hydrochloric acid precipitation.

On the other hand, in the process for separation of botulinum toxin 7S (low-molecular-weight botulinum toxin), the highest purification efficiency appeared when anion-exchange chromatography (HQ (binding mode or FT mode)) and cation-exchange chromatography (XS (binding mode)) were sequentially performed after each of the four pretreatment processes (the conventional process, UF following depth filtration, ammonium sulfate precipitation following depth filtration, and hydrochloric acid precipitation following depth filtration).

INDUSTRIAL APPLICABILITY

The novel method for producing the botulinum toxin according to the present invention makes it possible to fundamentally prevent the entry of animal-derived components, thereby ensuring increased safety. In addition, the use of the method of the present invention makes it possible to produce a high-purity botulinum toxin by a simple process, suggesting that the method is very economical and efficient. The botulinum toxin produced by the method of the present invention has a relatively high purity compared to botulinum toxins produced by conventional methods, and thus has an increased ability to act in a local area. Thus, the systemic circulation of the botulinum toxin, which can result in side effects, is reduced to increase the safety. Accordingly, the botulinum toxin of the present invention can be used for various purposes, including treatment of neuromuscular disorders, removal of wrinkles, and treatment of spastic hemiplegia and cerebral palsy.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for producing a botulinum toxin comprising:
   (a) treating a culture of a botulinum toxin-producing strain with acid to form a botulinum toxin-containing precipitate;
   (b) adding a buffer to the botulinum toxin-containing precipitate of step (a), and then clarifying by one or more method selected from the group consisting of depth filtration (DF), microfiltration (MF), ultrafiltration (UF), sterile filtration, and membrane chromatography (MC);
   (c) subjecting a botulinum toxin-containing solution of step (b) to hydrochloric acid precipitation, and then dissolving a precipitate resulting from the hydrochloric acid precipitation in a buffer; and
   (d) subjecting a hydrochloric acid precipitate solution of step (c) to anion-exchange chromatography (AEX), thereby purifying the botulinum toxin,
   wherein said method does not include enzymatic treatment using DNase and RNase.

2. The method of claim 1, wherein the botulinum toxin-producing strain is *Clostridium botulinum* or a mutant strain thereof.

3. The method of claim 1, wherein the botulinum toxin is selected from the group consisting of botulinum toxin serotypes A, B, C, D, E, F and G.

4. The method of claim 1, wherein the purified botulinum toxin is a botulinum toxin type A protein having a purity of at least 98%.

5. The method of claim 1, wherein the acid treating in step (a) is carried out by adding sulfuric acid or hydrochloric acid to the culture of the botulinum toxin-producing strain, thereby the culture reaches a pH of 3.0-4.5.

6. The method of claim 1, wherein the forming the botulinum toxin-containing precipitate in step (a) is performed once or more.

7. The method of claim 1, wherein the depth filtration (DF) in step (b) is carried out using a peristaltic pump, and a filter used for the depth filtration has a nominal pore size of 0.01-20 μm.

8. The method of claim 1, wherein hydrochloric acid precipitation in step (c) is performed once or more.

9. The method of claim 1, wherein hydrochloric acid precipitation in step (c) is carried out by adding hydrochloric acid to allow the botulinum toxin-containing solution to reach a pH of 2-5.

10. The method of claim 1, wherein the buffer in step (b) and step (c) is a sodium phosphate buffer.

11. The method of claim 10, wherein the sodium phosphate buffer in step (b) has a pH of 4.5-6.5, and the sodium phosphate buffer in step (c) has a pH of 6-7.

12. The method of claim 1, wherein the anion-exchange chromatography in step (d) is carried out in a solution with a pH of 2-9 and a conductivity of 2-40 mS/cm.

13. The method of claim 1, wherein the botulinum toxin in step (d) is collected as a botulinum toxin-containing fraction of flow-through (FT) fraction eluted from anion-exchange chromatography.

14. The method of claim 1, wherein the purified botulinum toxin has a form of 7S or 19S.

15. The method of claim 1, further comprising, after step (d):
   (e) adjusting the pH of a botulinum toxin-containing anion exchange chromatography fraction upward;
   (f) purifying the pH-adjusted anion exchange chromatography fraction resulting from step (e) by another anion exchange chromatography;
   (g) optionally, adding a buffer to the purified anion exchange chromatography fraction to dilute the botulinum toxin; and
   (h) purifying the diluted botulinum toxin resulting from step (f) using cation exchange chromatography (CEX).

16. The method of claim 15, wherein the upward adjustment of the pH of the anion-exchange chromatography fraction in step (e) is performed once or more.

17. The method of claim 15, wherein said optional step (g) is carried out.

18. The method of claim 17, wherein the buffer in step (g) is a sodium phosphate buffer.

19. The method of claim 18, wherein the sodium phosphate buffer in step (g) has a pH of 6.5-7.5.

20. The method of claim 15, wherein the upward adjustment of the pH in step (e) is carried out using one or more technique selected from the group consisting of UF diafiltration, pH titration, dialysis, and buffer exchange column chromatography.

21. The method of claim 20, wherein the upward adjustment of pH of the anion-exchange chromatography fraction in step (e) is carried out using Tris-HCl buffer.

22. The method of claim 21, wherein the Tris-HCl buffer in step (e) has a pH of 7.3-8.3.

23. The method of claim 15, wherein the anion-exchange chromatography in step (f) is carried out in a solution with a pH of 2-9 and a conductivity of 2-40 mS/cm.

24. The method of claim 15, wherein the botulinum toxin in step (f) is collected as a botulinum toxin-containing fraction of a flow-through (FT) fraction eluted from anion-exchange chromatography, or collected as a fraction containing the botulinum toxin bound to anion exchange chromatography resin.

25. The method of claim 15, wherein the cation-exchange chromatography in step (h) is carried out in a solution with a pH of 2-9 and a conductivity of 2-40 mS/cm.

26. The method of claim 15, wherein the botulinum toxin in step (h) is collected as a fraction containing the botulinum toxin bound to the cation-exchange chromatography resin.

27. The method of claim 15, wherein the finally purified botulinum toxin has a form of 7S.

* * * * *

UNITED STATES PATENT AND TRADEMARK OFFICE
CERTIFICATE OF CORRECTION

| | |
|---|---|
| PATENT NO. | : 10,619,143 B2 |
| APPLICATION NO. | : 15/758042 |
| DATED | : April 14, 2020 |
| INVENTOR(S) | : Kyoung-Yun Kim |

It is certified that error appears in the above-identified patent and that said Letters Patent is hereby corrected as shown below:

On the Title Page

Item (54) Title "METHOD AND PRODUCING BOTULINUM TOXIN" should be -- METHOD FOR PRODUCING BOTULINUM TOXIN --.

In the Specification

Column 9, Line 14: "0.1-8-82 m" should be -- 0.1-8 μm --.

Column 15, Line 34: "pH 6.46.6" should be -- pH 6.4-6.6 --.

Signed and Sealed this
Ninth Day of June, 2020

Andrei Iancu
*Director of the United States Patent and Trademark Office*